United States Patent [19]
Markart

[11] Patent Number: 5,904,898
[45] Date of Patent: May 18, 1999

[54] TEST STRIP

[75] Inventor: Ernst Markart, Munich, Germany

[73] Assignee: LRE Technology Partner GmbH, Munich, Germany

[21] Appl. No.: 09/040,062

[22] Filed: Mar. 17, 1998

[30] Foreign Application Priority Data

Sep. 4, 1997 [DE] Germany .......................... 197 14 674

[51] Int. Cl.$^6$ ................................................. G01N 21/84
[52] U.S. Cl. ................................ 422/61; 422/51; 422/58; 206/305
[58] Field of Search .................................. 422/58, 51, 61; 206/305

[56] References Cited

U.S. PATENT DOCUMENTS 3,346,464  10/1967  Ernst .......................................... 422/61
5,516,487  5/1996  Rosenthal et al. ......................... 422/61

Primary Examiner—Lyle A. Alexander
Assistant Examiner—Yolanda Wilkins
Attorney, Agent, or Firm—McCormick, Paulding & Huber

[57] ABSTRACT

In a test strip package having a plurality of test strips (20), each of which test strips has a test field (32) for evaluation by an optical measuring mechanism of a measuring device and including a container (12) for receiving the test strips (20) the container (12) is made as a rectangular closed flat envelope (12) for receiving a rectangular card (18), with the card (18) consisting of a plurality of test strips (20) which are separable from one another along tear lines (22). The measuring device comprises a device housing (38) with a test strip support surface (40) as well as a measuring optic system, an evaluation and control circuit and an indicator unit (42) contained in the housing, with the test strip surface (40) having a stop (44) for reception in a recess (30) in the envelope (12) as well as a stop (46) which is so positioned relative to the measuring optic system that upon the placement of a predetermined spot of a test strip (20) onto the stop (46) the test field (32) of the test strip (20) lies in the area of the measuring beam of the measuring optic system.

3 Claims, 5 Drawing Sheets

TEST STRIP

FIELD OF THE INVENTION

The invention concerns a test strip package with a plurality of test strips, each of which test strips has a test field capable of being evaluated by means of an optical or electrical current mechanism of a measuring device, and with a container for receiving the test strips.

BACKGROUND OF THE INVENTION

Test strips of the previously mentioned kind serve, for example, to quickly and in a simple way determine the concentration of certain substances in body fluids, for example, the sugar content of blood. Diabetic persons depending on circumstances must determine their blood sugar content several times a day and for this purpose must carry with them a measuring device and several other utensils, among others a container or magazine for test strips. These test strips must be used within a definite time period after the first opening of the container, since otherwise the chemicals in the test fields of the test strips so change that very likely a correct concentration measurement can no longer be made. Previously, it has been customary that the patient carries with him a small box with a certain number of test strips.

The invention has as its object the provision of a test strip package of the above-mentioned type which can be carried along with the person comfortably and with saving of space.

SUMMARY OF THE INVENTION

This object is solved in accordance with the invention in that the container is formed from a rectangular, closed flat envelope for receiving a rectangular card consisting of a plurality of test strips connected to one another by tear lines.

Such a test strip card protected by the envelope can be comfortably carried and even, as explained hereinafter, can be placed into the measuring device so that the test strip package does not have to be carried as a separate part along with the measuring device. Each needed test strip is then separated from the test strip card either before or after use.

Preferably, the envelope has a main section and a head section tearable from the main section along a prepared separation line running parallel to the tear lines, with the position of the separation line being so chosen that after the separation of the head section from the main section the test field of the first accessible test strip still lies in the main section. Thereby after the opening of the envelope, the test field is then protected against environmental influences until the needed test strip is pulled out of the envelope.

For the placement of the test strip package in the measuring device, it is practical if an edge area of the main section of the envelope has arranged on it at least one recess for the purpose of receiving an arresting element of the measuring device, with the arrangement being such that the test strip receiving space of the envelope is not disturbed or cut by the recess. Thereby the test strip card and the one test strip needed at the time can be pulled from the envelope with the envelope itself being held fast in the measuring device.

The separation line on the envelope can, for example, be predetermined by notches arranged opposite to one another on the longitudinal edges of the envelope in order to facilitate the tearing off of the head section from the main section at a predetermined position.

The tear lines between neighboring test strips preferably each include an elongated middle slot and perforation sections each extending from one end of the slot to the associated longitudinal edge of the card so that the tearing off a needed or already used test strip from the test strip card is facilitated.

A measuring device according to the invention for using one of the previously described test strip packages and for optically or by way of electrical current evaluating the test field of a test strip includes in known way a device housing with a test strip support surface as well as a measuring optic system or electrical contact mechanism arranged in the housing, an evaluation and control circuit and an indicator unit. The test strip support surface is in accordance with the invention formed to receive a test strip package of the above-described type and has arresting elements intended to be received in recesses in the envelope as well as a stop, which are so positioned relative to the measuring optic system or the electrical contact mechanism that with the positioning of a test strip at a pregiven position at the stop the test field of the test strip lies in the area of the measuring beam of the measuring optic system or in the area of the electrical contact mechanism. By the arresting element, the envelope is also held fast on the test strip support surface when a test strip is pulled out of the package. When a test strip is pulled out of the envelope to the mentioned stop, it is assured at the same time that the test field lies over the measuring optic system.

Preferably a sealing strip is arranged opposite to the test strip support surface and is biased in the direction of that surface so that it presses the edge regions of the open side of the main section of the envelope against the test strip support surface. So long as the test strips are not used, the test fields lie inside of the envelope. The envelope is pressed shut by the sealing strip so that the test field is protected against environmental influences, especially against dampness. The test strip is first pulled out so that the test field lies over the measuring optic immediately before the measurement.

The sealing strip can, for example, be arranged on a cover which is pivotally supported on the housing for movement about a pivot axis parallel to the test strip support surface, so that the test strip package can be conveniently laid onto the test strip support surface. After the closing of the cover, the sealing strip holds the test strip package firmly on the test strip support surface and closes the envelope.

To simplify the tearing of the test strips from the test strip card, a separating element having a separating edge can be so arranged on the housing that it is movable between a first position remote from the support surface and a second position closer to the support surface in which second position the separating edge runs parallel to a tear line of the test strip card. Preferably the separating element is so formed that it can be received in the above-described slot of a tear line. Thereby the separating element along with the tearing function also has the purpose of fixing the test strip card in a definite position on the test strip support surface. The test strip needed for the immediate measurement therefore is located by the separating element and the stop on the test strip support surface in an exactly predetermined position and is held fast by the separating element in this position as well as by the fact that it is still connected with the test strip card pressed by the sealing lip against the test strip support surface.

Preferably the separating element is arranged on a pivotal lever, for example, on the cover carrying the sealing strip.

BRIEF DESCRIPTION OF THE DRAWINGS

Further features and advantages of the invention will be apparent from the claims and the following description describing an exemplary embodiment of the invention by way of the accompanying drawings. The drawings show:

DETAILED DESCRIPTION OF THE PREFERRED EMBODIMENTS

Figure 1:
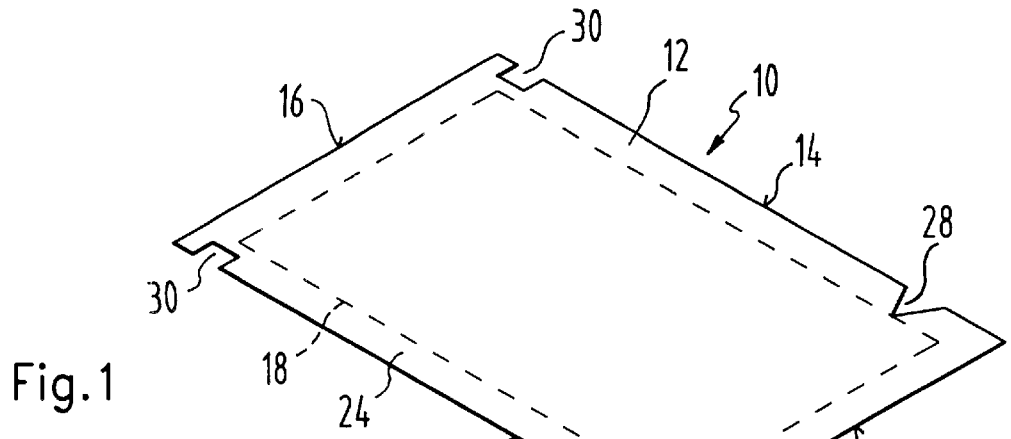
FIG. 1—a schematic perspective view of a test strip package.

A test strip package is illustrated in FIG. 1 and indicated generally by the reference number 10. It comprises a rectangular flat envelope or bag 12 which is closed along its longitudinal edges 14 and along its transverse edges 16. It consists of two material webs or a single folded material web with the originally open longitudinal and transverse edges 14 and 16 being glued or welded and with the material webs being air and moisture impermeable.

The envelope 12 serves to receive a rectangular test strip card 18, indicated by broken lines in FIG. 1, with a plurality of test strips 20 which are connected to one another along tear lines 22. The test strip card 18 is explained further in more detail below.

The envelope 12 comprises a main section 24 and a head section 26 separable from the main section 24. The separation line along which the head section 26 is separated from the main section 24 is marked by two notches 28 lying opposite to one another in the longitudinal edges 14 of the envelope 12.

Near the end of the envelope which is opposite from the head section 26 are formed two rectangular recesses 32 in the longitudinal edges 14, the function of which recesses is explained below in more detail in connection with the description of the measuring device.

Figure 2:
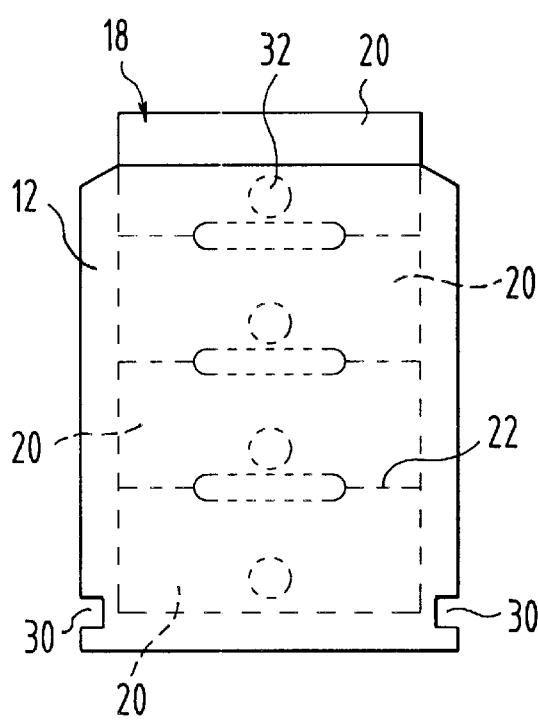
FIG. 2—a view of a test strip package corresponding to FIG. 1 after the tearing off of the head section, FIG. 3—a schematic perspective view of a measuring device embodying the invention for an optical evaluation and for use with the test strip package illustrated in FIGS. 1 and 2, the device being shown with an opened cover, FIG. 4—a view corresponding to FIG. 3 wherein the cover of the measuring device is closed, FIG. 5—a schematic perspective view of a measuring device according to the invention intended for an evaluation by way of electrical current measurement, FIG. 6—a view corresponding to FIG. 5 with the cover of the measuring device closed, and FIG. 7—a schematic plan view of a portion of the test strip support of a modified embodiment of a measuring device according to the invention.

According to FIG. 2, each test strip 20 has a test field 32 onto which a body fluid, for example a drop of blood, can be dropped and subsequently optically analyzed in a way known in itself. If the head section 26 is torn from the main section 24 of the envelope 12, the first test strip 20 of the test strip card extends just so far from the main section 24 of the envelope 12 that it can be grasped (FIG. 2). The test field 32, however, lies still protected in the main section 24 of the envelope 12.

Each tear line 22 between two test strips 20 consists of a middle longitudinal slot 34 and perforation lines 36 extending from the ends of the slot to the longitudinal edges 14.

The use of the previously described test strip package 10 will now be explained in connection with FIGS. 3 and 4. The measuring device includes a housing indicated generally at 38 with a support surface 40 for the test strip package 10. The housing contains in a way known in itself a measuring optic system and an evaluation and control circuit, both of which are not illustrated, as well as an indicator unit 42. The measuring beam of the measuring optic system passes through an opening formed in the support surface 40 below the test field 32 of the test strip 20 illustrated in FIGS. 3 and 4 which is pulled entirely out of the envelope 12. A grip depression 43 is formed in the support surface 40 so that the test strip can easily be grasped.

Figure 3:
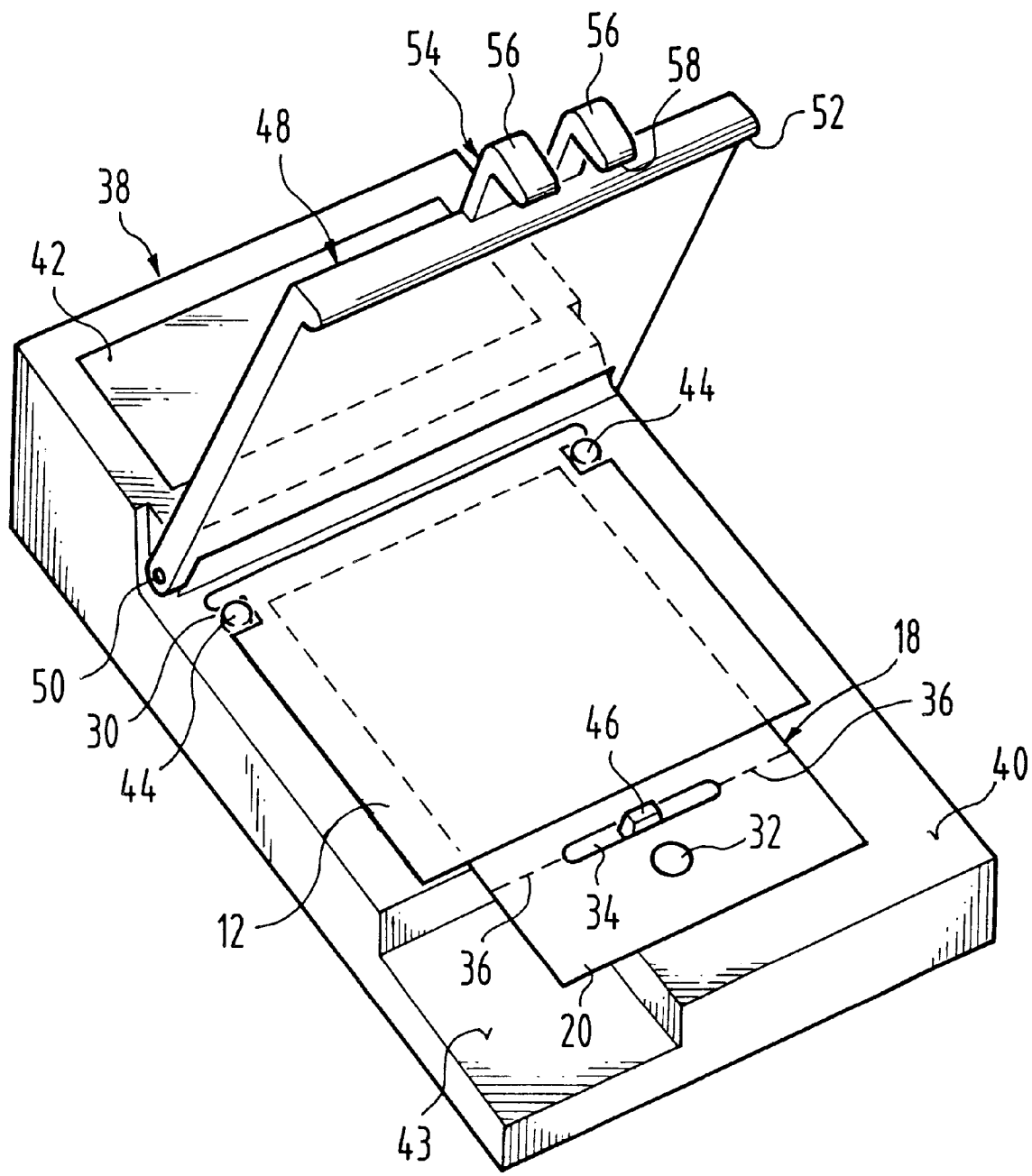

As can be seen in FIG. 3, the test strip package is so positioned on the support surface 40 that arresting pins 44, which are provided on the support surface 40 near the indicator unit 42, are received in the rectangular notches 30 in envelope 12. In this way the test strip package 10 is fixed to the support surface 40. The envelope 12 remains at its place when the test strip card 18 is pulled from the envelope 12, until a stop or nose 46 arranged on the test strip support surface 40 enters the slot 34 behind the first pulled-out test strip, as illustrated in FIG. 3. In this position, which is repeated in FIG. 4, the test field 22 lies exactly over the opening for the measuring beam.

A lid or cover 48 is pivotally supported on the housing 38 for movement about a pivot axis 50 parallel to the support surface 40. The cover can, therefore, be pivoted between the first position illustrated in FIG. 3, in which the support surface 40 is freely accessible, in order to place the envelope 12 onto the support surface 40 or to remove it therefrom and a second position (FIG. 4) in which the support surface 40 is partially covered. The cover 40 can be biased to this second position by suitable non-illustrated means so that it lies firmly onto the support surface 40.

On its free edge remote from the pivot axis 40, the cover 48 has a sealing lip 52 which in the second position of the cover 48 engages the envelope 12 of the test strip package 10 near the open edge of the main section 24. The sealing lip 52 on one hand holds the envelope 12 closed and on the other hand holds the test strip package 10 firmly onto the support surface 40.

The cover 28 further carries at its free end remote from the pivot axis 50 two L-shaped elements 54 the free short leg of each of which is formed as a wedge shaped separating element 56 having a free separating edge 58. The arrangement of the elements 54 is so designed that upon shutting of the lid 48 the separating elements 56 are exactly received in the slot 34 of the tear line 22 behind the test strip 20 extending fully from the envelope 12. Thereby, on one hand the test strip card is further fixed onto the support surface 40. On the other hand, the portion of the test strip card remaining in the envelope 12 is held fast when the entirely pulled-out test strip 20 is torn off after the carrying out of the measurement. The arrangement can also be so designed that the wedge shaped separating elements can be pressed into a non-illustrated recess in the test strip support surface to thereby separate the test strips from another.

A served person in using the measuring device goes through the following procedure:

First, the device is prepared in a known way for a measurement. After this, the cover 48 is opened. The head section 26 is separated from the envelope 12 of the test strip package 10 and the main section 24 is so placed onto the support surface 40 that the arresting pins 44 are received in the notches 30. The portion of the test strip card 18 extending out of the main section 24 lies prepared for grasping over the gripping depression 43. The cover 50 is then closed. With this, the device is loaded and the test strip card is protected from moisture. When a measurement is to be carried out, the cover 50 is opened and the test strip 20 is pulled so far out of the envelope 20 that the nose 46 can enter the slot 34 directly following the pulled-out test strip 20. The position of the nose 46 is so chosen that in this position of the test strip card 18, the test field 22, which was previously protected in the envelope 12, lies over the measuring opening. In this position, an empty measurement of the test field 32 is carried out. After this, the body fluid to be analyzed is dropped onto the test field and the actual measurement is carried out. The measured value delivered by the evaluation circuit appears on the indicator unit 42. Then the cover 48 is closed, whereupon the separating elements 56 enter the slot 34 behind the entirely pulled-out test strip 20. The used test strip 20 can then be removed. The previously described measuring process can be repeated so long as test strips are at hand in the envelope. After that, a new test strip package must be inserted.

Figure 7:
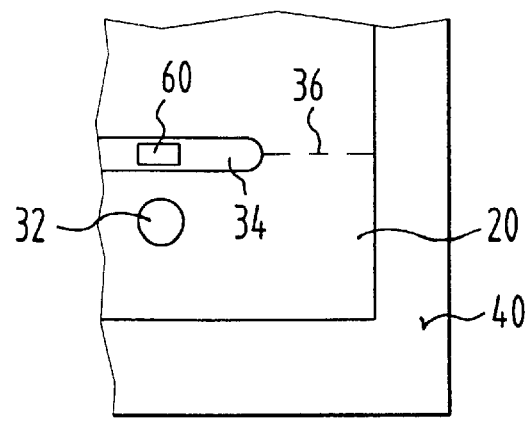

Additionally or alternatively to the positioning of the test strip 20 by means of the nose 46, it can also be determined by means of the measuring optic system whether the test field 32 lies exactly over the measuring opening. For the same purpose, a supplemental optic system 60 can also be provided (FIG. 7), which for example senses an aperture such as the slot 34 when the test field 32 lies over the measuring optic system. This case is illustrated in FIG. 7. Likewise the supplemental optic system can respond to a mark on the test strip with the mark and the supplemental optic system being so arranged relative to the test field and the measuring optic system that upon sensing of the mark by the supplemental optic system the test field lies over the measuring optic system.

Figure 4:
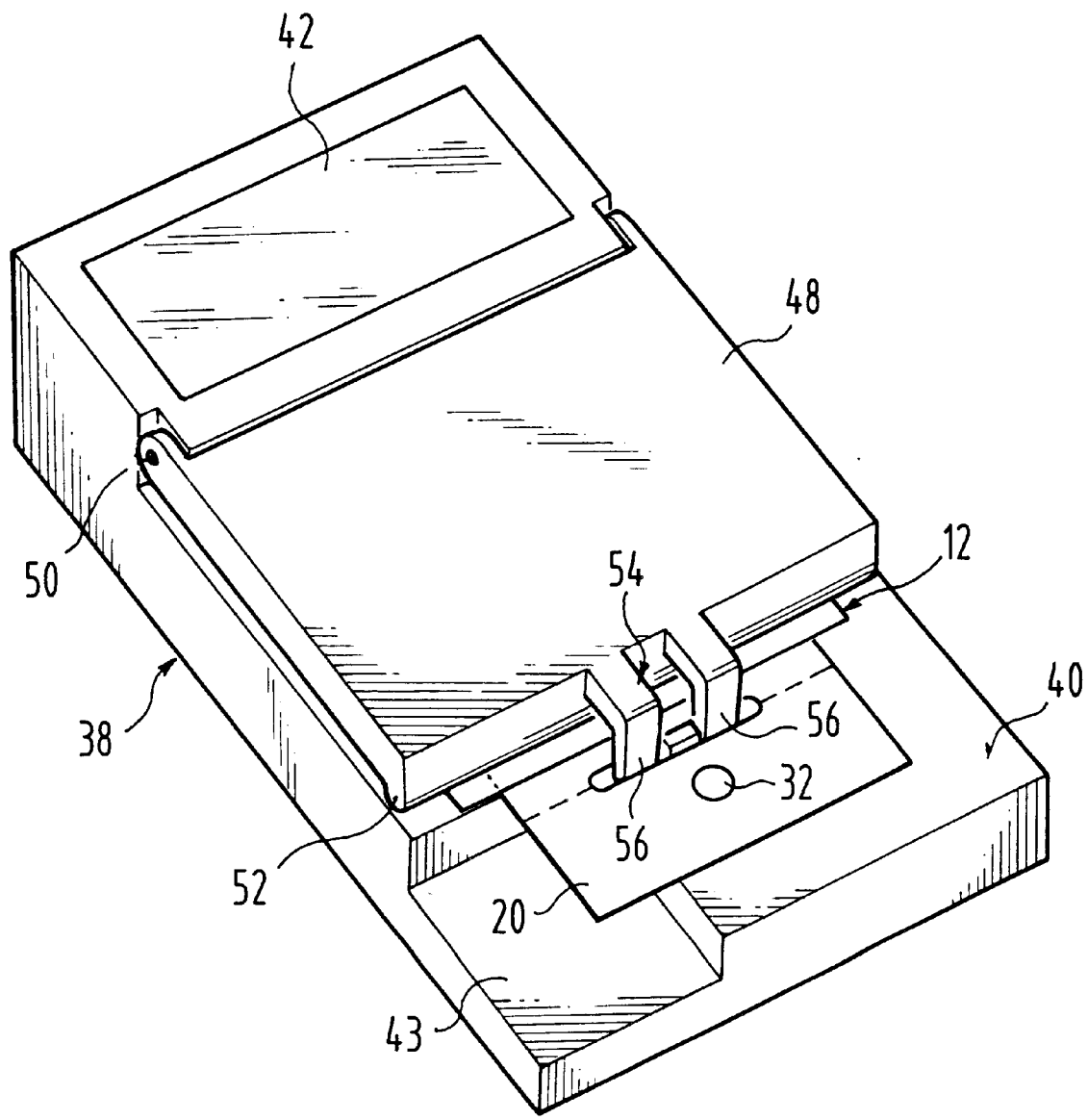
Figure 5:
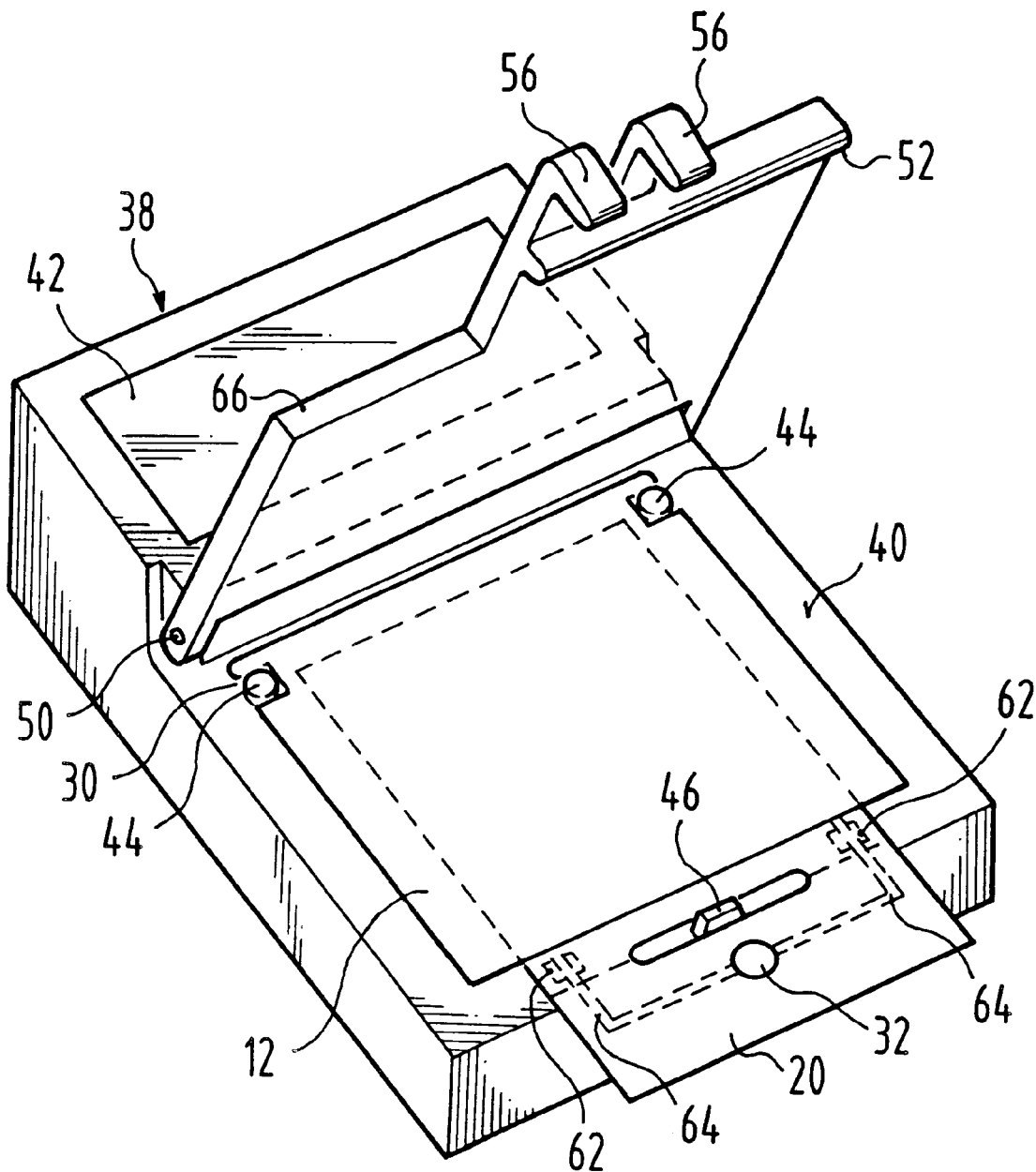
Figure 6:
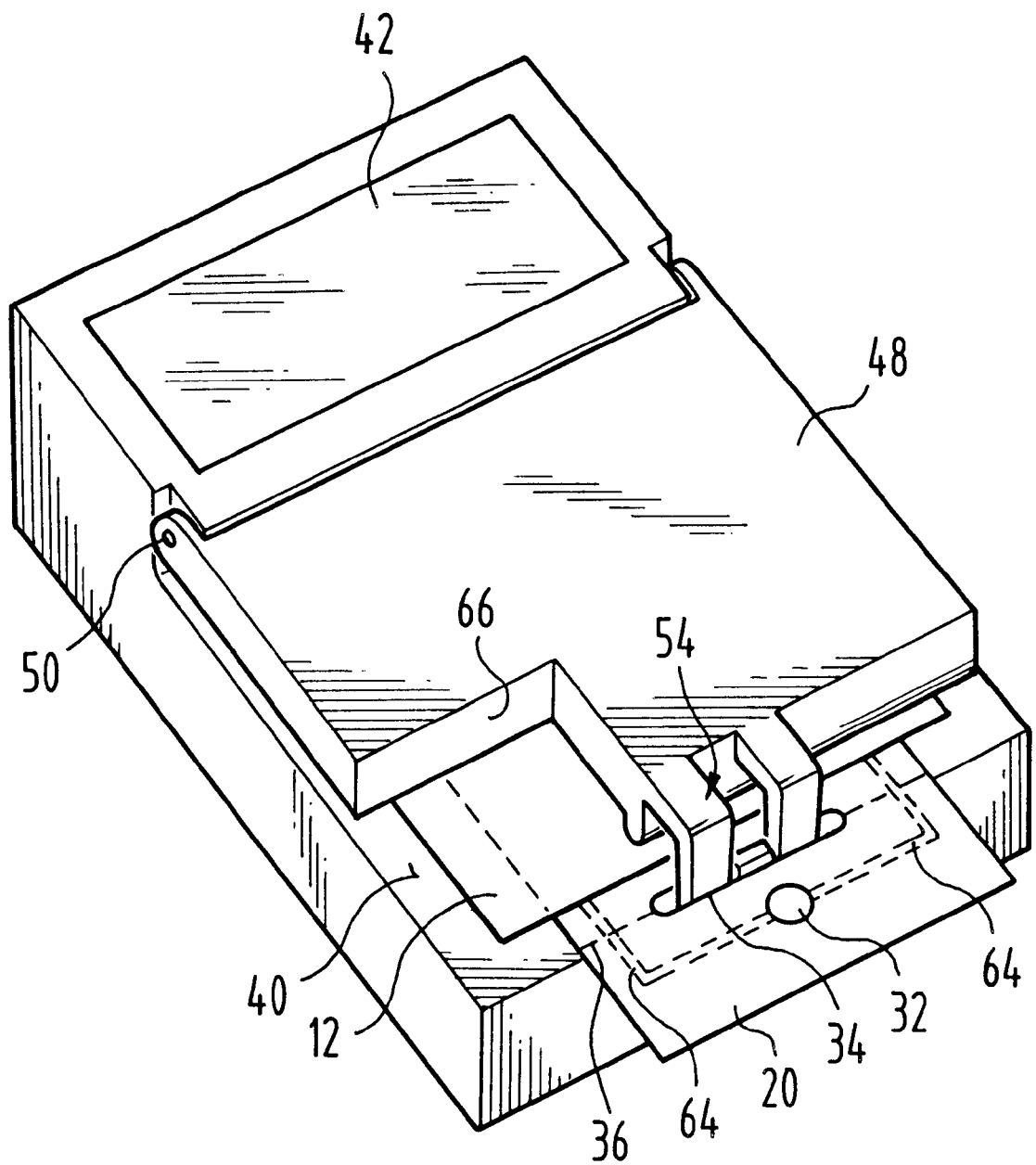

A further embodiment of the inventive measuring device is illustrated in FIGS. 5 and 6. The measuring device shown there is suited for an electrical current type evaluation of the test strip. Parts similar to those of the measuring device of FIGS. 3 and 4 are indicated by the same reference numbers and are not explained again.

The essential difference to the measuring device according to FIGS. 3 and 4 resides in that the device has no measuring optic system but instead has an electrical contact mechanism with contact elements 62 arranged in the test strip support surface 40, which contact elements can come into contact with contact paths 64 on the test strips 20 when the test strip card 18 lies on the test strip support surface 40. The housing 38 is shortened in comparison to the housing illustrated in FIGS. 3 and 4. The nose 46 is located on the forward edge of the housing 38. A recess 66 is provided in the cover 48, which recess facilitates grasping of the test strip 20 to be pulled out of the envelope 12.

The preparation of the measuring device takes place in the above-described way. After the test strip 20 is positioned by means of the nose 42, the fluid to be analyzed is dropped onto the test field 32. With the help of the contact elements 62, the current flowing over the test field 32 can then be measured. The measured current strength can then be evaluated for determining the concentration of the sought substance. The test strip 20 extending outwardly from the closed device can then be torn off or can be separated by the insertion of the separating element 56 into the slot 34.

Also, with the device of FIGS. 5 and 6 a supplemental optic system can be provided for precisely positioning the test strip.

In both embodiments, the supplemental optic system, or in the embodiment according to FIGS. 3 and 4 the measuring optic system, can be formed as a sending and/or receiving apparatus for sending or receiving data. In this way, for example, stored measured values can be read out of the measuring device. Reversely, the measuring device can receive in this way characteristic data and other information about the test strips to be used.

I claim:

1. A test strip package with a plurality of test strips (20) each of which test strips has a test field (32) evaluatable by means of an optical or electrical current measuring mechanism of a measuring device, said test package comprising:

a container formed as a rectangular closed flat envelope (12), and a rectangular card (18) received in said envelope, said card (18) having a number of said test strips (20) connected with one another along tear lines (22), said envelope (12) including a main section (24) and a head section (22) tearable from said head section along a tearable separation line, said separation line running parallel to said tear lines (22) and being so positioned that, after the separation of the head section (26) from the main section (24) the test field (32) of the first accessible test strip (20) of the test strip card (18) still lies within the main section (24) of the envelope (12).

2. A test strip package according to claim 1, wherein:

recesses (30) are arranged in the edge regions of said main section (24) of the envelope (12) at least one of which recesses is intended to receive an arresting element (44) of the measuring device, said recesses not touching upon or cutting the test strip receiving space of said envelope.

3. A test strip package according to claim 2, wherein:

said separation line is defined by two notches (28) located opposite to one another in the longitudinal edge areas (14) of the envelope (12).

* * * * *